United States Patent
Passaniti et al.

(10) Patent No.: US 11,598,649 B2
(45) Date of Patent: Mar. 7, 2023

(54) SYSTEM AND METHOD FOR DETECTING STEPS WITH DOUBLE VALIDATION

(71) Applicant: STMicroelectronics S.r.l., Agrate Brianza (IT)

(72) Inventors: Fabio Passaniti, Syracuse (IT); Enrico Rosario Alessi, Catania (IT)

(73) Assignee: STMICROELECTRONICS S.r.l., Agrate Brianza (IT)

( * ) Notice: Subject to any disclaimer, the term of this patent is extended or adjusted under 35 U.S.C. 154(b) by 63 days.

(21) Appl. No.: 17/017,414

(22) Filed: Sep. 10, 2020

(65) Prior Publication Data

US 2021/0081032 A1 Mar. 18, 2021

(30) Foreign Application Priority Data

Sep. 12, 2019 (IT) .......................... 102019000016142

(51) Int. Cl.
*G01C 22/00* (2006.01)
*G01P 15/08* (2006.01)
(Continued)

(52) U.S. Cl.
CPC ............ *G01C 22/006* (2013.01); *A61B 5/112* (2013.01); *A61B 5/681* (2013.01); *A61B 5/721* (2013.01);
(Continued)

(58) Field of Classification Search
CPC ...... G01C 22/006; G06V 40/25; A61B 5/681; A61B 5/721; G01P 15/08; G01P 2015/0865; G06K 9/00543; G06N 20/00
See application file for complete search history.

(56) References Cited

U.S. PATENT DOCUMENTS

| 5,844,415 A | 12/1998 | Gershenfeld et al. |
| 6,253,075 B1 * | 6/2001 | Beghtol ................. H04W 4/20 |
| | | 455/567 |

(Continued)

FOREIGN PATENT DOCUMENTS

| EP | 1 770 368 A1 | 4/2007 |
| EP | 1 770 369 A1 | 4/2007 |

(Continued)

OTHER PUBLICATIONS

Amoruso et al., "An improved model of man for ESD applications," *Journal of Electrostatics* 49:225-244, 2000.
(Continued)

*Primary Examiner* — Nicholas Augustine
(74) *Attorney, Agent, or Firm* — Seed Intellectual Property Law Group LLP

(57) ABSTRACT

A system for detecting steps of a user includes processing circuitry and a sensor configured to detect a variation of electrostatic charge of the user during a step of the user and generate a charge-variation signal. An accelerometer is configured to detect an acceleration as a consequence of the step and generate an acceleration signal. The processing circuitry is configured to: acquire the charge-variation signal; acquire the acceleration signal; detect, in the charge-variation signal, a first characteristic identifying the step; detect, in the acceleration signal, a second characteristic identifying the step. If both of the first and second characteristics have been detected, the presence of the step can be validated.

29 Claims, 6 Drawing Sheets

(51) Int. Cl.
  *A61B 5/11* (2006.01)
  *A61B 5/00* (2006.01)
  *G06K 9/00* (2022.01)
  *G06V 40/20* (2022.01)
  *G06N 20/00* (2019.01)

(52) U.S. Cl.
  CPC .......... *G01P 15/08* (2013.01); *G06K 9/00543* (2013.01); *G06V 40/25* (2022.01); *G01P 2015/0865* (2013.01); *G06N 20/00* (2019.01)

(56) References Cited

U.S. PATENT DOCUMENTS

| | | | |
|---|---|---|---|
| 6,477,117 B1* | 11/2002 | Narayanaswami | G04G 21/04 368/251 |
| 2002/0164006 A1* | 11/2002 | Weiss | H04M 7/003 379/201.01 |
| 2004/0169674 A1* | 9/2004 | Linjama | G06F 1/1626 715/702 |
| 2007/0273648 A1* | 11/2007 | Fussinger | G06F 3/0338 345/161 |
| 2009/0082994 A1 | 3/2009 | Schuler et al. | |
| 2010/0177598 A1* | 7/2010 | Zhang | G04R 20/20 368/10 |
| 2011/0022196 A1* | 1/2011 | Linsky | G06F 3/011 700/85 |
| 2011/0151850 A1* | 6/2011 | Haaparanta | H04M 1/2745 455/415 |
| 2012/0020190 A1* | 1/2012 | Suzusho | G04G 13/025 368/10 |
| 2013/0085700 A1 | 4/2013 | Modi et al. | |
| 2013/0085711 A1 | 4/2013 | Modi et al. | |
| 2013/0321340 A1* | 12/2013 | Seo | G06F 3/04883 345/174 |
| 2014/0036643 A1* | 2/2014 | Messenger | G01C 22/00 368/251 |
| 2014/0051406 A1* | 2/2014 | Kim | H04W 4/16 455/414.1 |
| 2014/0111415 A1* | 4/2014 | Gargi | G06F 3/0346 345/156 |
| 2014/0127665 A1* | 5/2014 | Arai | G09B 7/06 434/362 |
| 2014/0135612 A1 | 5/2014 | Yuen et al. | |
| 2014/0180595 A1* | 6/2014 | Brumback | G16H 40/67 702/19 |
| 2014/0197946 A1* | 7/2014 | Park | A61B 5/02055 340/539.11 |
| 2014/0198628 A1* | 7/2014 | Yang | G04G 13/02 368/262 |
| 2014/0205076 A1* | 7/2014 | Kumar | H04M 7/0033 379/142.01 |
| 2014/0232516 A1 | 8/2014 | Stivoric et al. | |
| 2014/0247147 A1 | 9/2014 | Proud | |
| 2014/0267094 A1* | 9/2014 | Hwang | G06F 3/0488 345/173 |
| 2014/0269224 A1* | 9/2014 | Huh | G04G 13/021 368/73 |
| 2014/0278139 A1 | 9/2014 | Hong et al. | |
| 2014/0320387 A1* | 10/2014 | Eriksson | G06F 3/017 345/156 |
| 2014/0372896 A1* | 12/2014 | Raman | G06F 3/017 715/741 |
| 2015/0017956 A1* | 1/2015 | Jeong | G06F 3/0484 455/414.1 |
| 2015/0094031 A1* | 4/2015 | Liu | H04M 3/436 455/412.2 |
| 2015/0181398 A1* | 6/2015 | Garbin | H04M 3/42348 455/417 |
| 2016/0048211 A1* | 2/2016 | Raffle | G06F 3/013 715/863 |
| 2016/0183869 A1* | 6/2016 | Oh | A61B 5/681 600/595 |
| 2016/0239354 A1* | 8/2016 | Shen | H04M 1/72451 |
| 2016/0342781 A1 | 11/2016 | Jeon | |
| 2017/0011210 A1* | 1/2017 | Cheong | A61B 5/681 |
| 2019/0113364 A1 | 4/2019 | Khedr et al. | |
| 2019/0253519 A1* | 8/2019 | Milosevic | H04L 67/535 |

FOREIGN PATENT DOCUMENTS

| | | |
|---|---|---|
| EP | 2 980 609 A1 | 2/2016 |
| KR | 10-2011-0061750 A | 6/2011 |
| WO | 2015/184206 A1 | 12/2015 |

OTHER PUBLICATIONS

Ficker, "Electrification of human body by walking," *Journal of Electrostatics* 64:10-16, 2006.

Kurita, "Development of Non-Contact Measurement System of Human Stepping," SICE Annual Conference 2008, Aug. 20-22, 2008, The University Electro-Communications, Japan, 4 pages.

"Galvanic Skin Response—CHRIS3000," retrieved from www.chris3000.com/galvanic-skin-response/, published Feb. 5, 2017, 6 pages.

* cited by examiner

SYSTEM AND METHOD FOR DETECTING STEPS WITH DOUBLE VALIDATION

BACKGROUND

Technical Field

The present disclosure relates to a system and to a method for detecting a step of a user.

Description of the Related Art

Devices are known that are used for continuous monitoring of the body of a user in the environment and in free-living conditions. A wide range of sensors, for example adapted to detect the acceleration, electrical resistance of the skin, temperature of the skin, flow of heat irradiated, and heart rate, are used in various combinations for determining or deriving parameters such as rate of caloric combustion, type and level of activity, and state of sleep. Said devices use sophisticated algorithms for integrating various streams of data acquired in order to determine output parameters with the best precision possible (e.g., calories burnt, type of physical activity, etc.). Further sensors, for detecting additional parameters, supply further data to the algorithms to improve precision thereof.

In particular, as regards the counting of steps, it is known to use triaxial accelerometers (frequently integrated in portable devices) adapted to supply a signal of acceleration along three orthogonal axes and process the acceleration signal by step-recognition algorithms in order to identify specific signal variations (or patterns) that can be correlated to execution of a step by the user. However, processing of the acceleration signal is calibrated on an "average" or "standard" user and does not take into account specific physical conditions or needs (even only temporary ones) that may arise. For instance, on account of physical problems, the user could make very short steps, or steps with a gait different from that of the average user taken as reference during calibration of the step-recognition algorithm. Likewise, the movement of arms, used by the software installed on board wearable devices (e.g., smartwatches), might not be indicative of a step in the case where the user had problems in such a movement. Other unforeseeable conditions could moreover prevent a correct counting of the steps.

Electrical-field sensors are used as an alternative or in addition to accelerometric sensors for determining the activity of a user, or as an aid to interpret the signals generated by other sensor devices.

Electric charge is a fundamental component of nature. Electrons of an element are easily transferred to another element in conditions of direct contact between the elements or at a distance. When the charge is transferred between two electrically insulated objects, a static charge is generated so that the object with an excess of electrons is negatively charged and the object with a deficit of electrons is positively charged.

The electrons move within an object in various ways according to whether the object is a conductive or an insulating object. In a conductor, the electrons are more or less evenly distributed throughout the material and can easily move as a result of the effect of the external electrical fields. In an insulator, the charge exists mainly on the surface. The charge may, however, be mobile, according to the properties of the material and other environmental factors.

Devices that detect variation of the electrical field generated by a human during his movements, or that exploit a detection of a capacitive type are known. Technologies that use this latter type of detection include, for example, touchscreens, systems detecting the position of the occupants of motor vehicles, and devices for determining the position, orientation, and the mass of an object, such as for example described in the patent document No. U.S. Pat. No. 5,844,415, which regards a device for detecting electrical field in order to determine the position, the distribution of mass and the orientation of an object within a defined space by arranging a plurality of electrodes within the space defined. The above technical solution could moreover be used for recognizing the gestures of a user, the position and orientation of his hand, for example for interactive use with a processing system instead of a mouse or joystick.

The patent document No. US2014/232516 proposes the use of an electrostatic-charge sensor for deriving from a field or a capacitance sensor a physiological parameter or the activity of a user, such as walking, riding a bicycle or expending energy.

None of the documents referred to above, however, teaches a method for counting steps by exploiting a sensor for detecting variation in electrical or electrostatic charge.

The scientific paper by K. Kurita, "Development of Non-Contact Measurement System of Human Stepping", SICE Annual Conference 2008, Japan, illustrates a system and a method for counting steps made by a subject by exploiting a contactless technique. This technique envisages detecting the current of electrostatic induction, generated as direct consequence of the movement of the subject in the environment, through an electrode set at a distance of 1.5 m from the subject. However, the experiment illustrated in this document is conducted in ideal conditions, and is a mere demonstration of the applicability of the technology to the counting of steps. This document does not teach a technique that can be applied in real-life conditions, in which the subject, in addition to making steps, performs a plurality of other activities, each of which causes a variation of the electrostatic charge detected by the sensor. In these conditions, detection of the signal components due exclusively to the steps of the subject is complex and does not guarantee high reliability on the correctness of detection and consequent counting.

BRIEF SUMMARY

According to the present disclosure a system and a method for detecting a step of a user are provided.

In some embodiments, the present disclosure facilitates or provides systems and methods in which a double validation is facilitated by a sensor for detecting variation of electrostatic charge and by an accelerometer prior to validation of execution of the step.

Embodiments of the present disclosure make up for or otherwise overcome the shortcomings of the prior art by providing a system for detecting steps (or a step-counter system) that is inexpensive and reliable and involves a low computational load.

In one or more embodiments, the present disclosure provides a system for detecting a step of a user that includes processing circuitry, a sensor, and an accelerometer. The sensor is coupled to the processing circuitry and configured to detect a variation of electrostatic charge of the user during execution of a step by the user and generate a charge-variation signal. The accelerometer is coupled to the processing circuitry and configured to detect an acceleration as a consequence of the step of the user and generate an acceleration signal. The processing circuitry is configured to: acquire the charge-variation signal; acquire the acceleration signal; detect, in the charge-variation signal, a first characteristic identifying the step of the user; detect, in the acceleration signal, a second characteristic identifying the step of the user; and validate the execution of the step by the user in response to detecting both the first and the second characteristics.

In one or more embodiments, the present disclosure provides a portable electronic device that includes the system for detecting a step of a user.

In one or more embodiments, the present disclosure provides a method for detecting a step of a user that includes: supplying a charge-variation signal by a sensor configured to detect a variation of electrostatic charge of the user during the execution of a step by the user; supplying an acceleration signal by an accelerometer coupled to processing circuitry and configured to detect an acceleration as a consequence of the step of the user; detecting, in the charge-variation signal, a first characteristic identifying the step of the user; detecting, in the acceleration signal, a second characteristic identifying the step of the user; and validating the execution of the step by the user in response to detecting both of the first and second characteristics.

BRIEF DESCRIPTION OF THE SEVERAL VIEWS OF THE DRAWINGS

For a better understanding of the disclosure, embodiments thereof are now described purely by way of non-limiting example and with reference to the attached drawings, wherein.

DETAILED DESCRIPTION

Figure 1:
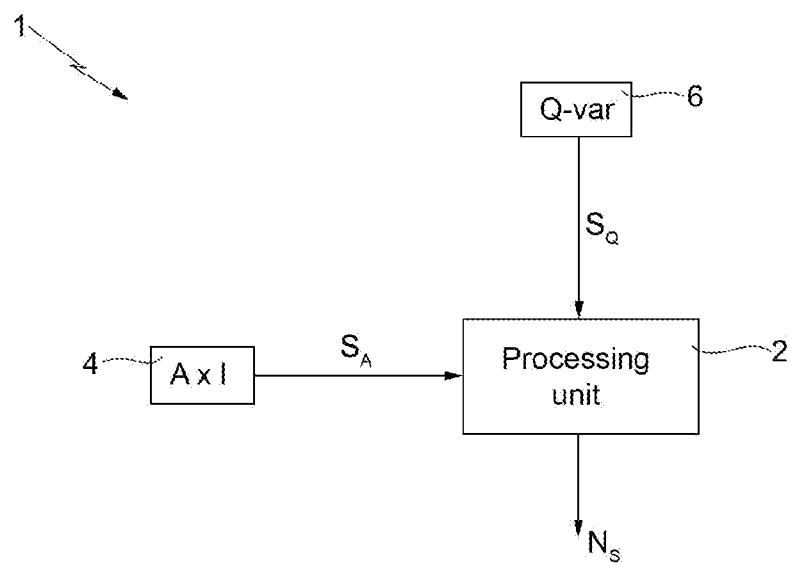
FIG. 1 is a schematic illustration of a system for detecting steps including an accelerometer and a sensor for detecting variation of electric charge, according to one embodiment of the present disclosure.

FIG. 1 is a schematic illustration of a step-detection system 1 according to one aspect of the present disclosure. The step-detection system 1 comprises processing circuitry 2 (which may be referred to herein as a processing unit 2), an accelerometer 4 coupled to the processing unit 2, and a sensor 6 for detecting variation of electrostatic charge coupled to the processing unit 2.

The accelerometer 4 is configured, in a per se known manner, for detecting at least a component of acceleration along a vertical acceleration axis (axis Z, i.e., parallel to the direction of the force of gravity vector).

The processing unit 2 receives an acceleration signal $S_A$ from the accelerometer 4 and a charge-variation signal $S_Q$ from the sensor 6 for detecting variation of electrostatic charge and generates, as a function of the acceleration signal $S_A$ and of the charge-variation signal $S_Q$, the number of steps $N_S$ of a user (not illustrated).

The accelerometer 4 is preferably a triaxial accelerometer, i.e., adapted to detect the acceleration along three mutually orthogonal directions X, Y, Z. The accelerometer 4 is, for example, an integrated sensor of semiconductor material, provided in MEMS technology, of a type in itself known and for this reason not described in detail. In use, according to one embodiment, the accelerometer 4 detects the component along the sensing axis Z of the vertical acceleration generated when the step is made, and produces a corresponding acceleration signal $S_A$ (FIG. 3b). It is in any case evident that, in general, the present disclosure may use also the acceleration information on the other sensing axes of the accelerometer (axis X and/or axis Y).

The processing unit 2 is, for example, a microcontroller or an MLC (Machine-Learning Core) residing in the ASIC (Application-Specific Integrated Circuit) integrated in the MEMS.

The step-detection system 1 is formed, for example, in integrated form on a same printed-circuit board, or in integrated form within a MEMS device that houses it. In fact, it is possible to envisage a device that several sensors ("combo"), in addition to the three axes X, Y, Z of the accelerometer 4, dedicated channels may also exist for other detections (made, for example, by a gyroscope, a temperature sensor, etc.), including the sensor for detecting variation of electrostatic charge and consequently.

The step-detection system 1 forms, in one embodiment (FIG. 5), part of a device 1 wearable by a user, for example on his wrist, so as to be fixed with respect to the body of the user and in electrical contact with a region of the body of the user (e.g., the wrist). The device 1 therefore is affected both by the vertical accelerations (and, optionally, along the other axes, as mentioned previously) that arise during a step, caused by impact of the feet on the ground, and by the variation of electrostatic charge due to the movement of the user (in particular, due to the steps made).

Figure 2:
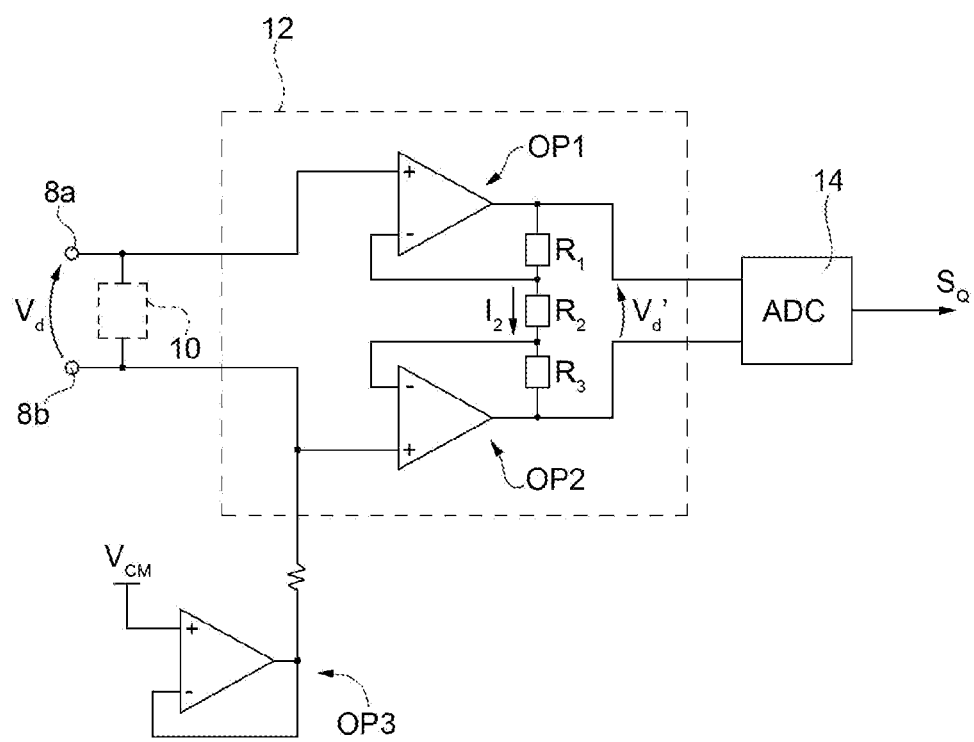
FIG. 2 illustrates an embodiment of the sensor for detecting variation of electric charge, which can be worn by a user.

FIG. 2 illustrates by way of non-limiting example an embodiment of a sensor 6 for detecting variation of electrostatic charge. The sensor 6 for detecting variation of electrostatic charge comprises a pair of input electrodes 8a, 8b, couplable to a portion 10 of the body of a user. In particular, the sensor 6 for detecting variation of electrostatic charge of FIG. 2 is configured to be set in direct contact with the portion of the body of a user.

The pair of input electrodes 8a, 8b represents the differential input of an instrumentation amplifier 12 and, in use, receives an input voltage Vd.

The instrumentation amplifier 12 is basically constituted by two operational amplifiers OP1 and OP2. A biasing stage (buffer) OP3 is used for biasing the instrumentation amplifier 12 at a common-mode voltage VCM.

The inverting terminals of the operational amplifiers OP1 and OP2 are connected together by a resistor $R_2$. Since the two inputs of each operational amplifier OP1, OP2 should be at the same potential, the input voltage Vd is applied also the ends of $R_2$ and causes, through this resistor $R_2$, a current equal to $I_2 = Vd/R_2$. This current $I_2$ does not come from the input terminals of the operational amplifiers OP1, OP2 and therefore traverses the two resistors $R_1$ connected between the outputs of the operational amplifiers OP1, OP2, in series to the resistor $R_2$. Therefore, the current $I_2$, by traversing the series of the three resistors $R_1$–$R_2$–$R_1$, produces an output voltage Vd' given by Vd'=$I_2$(2$R_1$+$R_2$)=Vd(1+2$R_1$/$R_2$). Consequently, the total gain of the circuit of FIG. 2 will be Ad=(+2$R_1$/$R_2$). The differential gain depends upon the value of the resistor $R_2$ and can therefore be modified by acting on the resistor $R_2$.

The differential output Vd', which is therefore proportional to the potential Vd between the input electrodes 8a, 8b, is supplied at input to an analog-to-digital converter 14, which supplies at output the charge-variation signal $S_Q$ to be sent the processing unit 2. The charge-variation signal $S_Q$ is, for example, a high-resolution (16-bit or 24-bit) digital stream. The analog-to-digital converter 14 is optional in so far as the processing unit 2 can be configured to work directly on the analog signal or can itself comprise an analog-to-digital converter adapted to convert the signal Vd'.

Figure 3A:
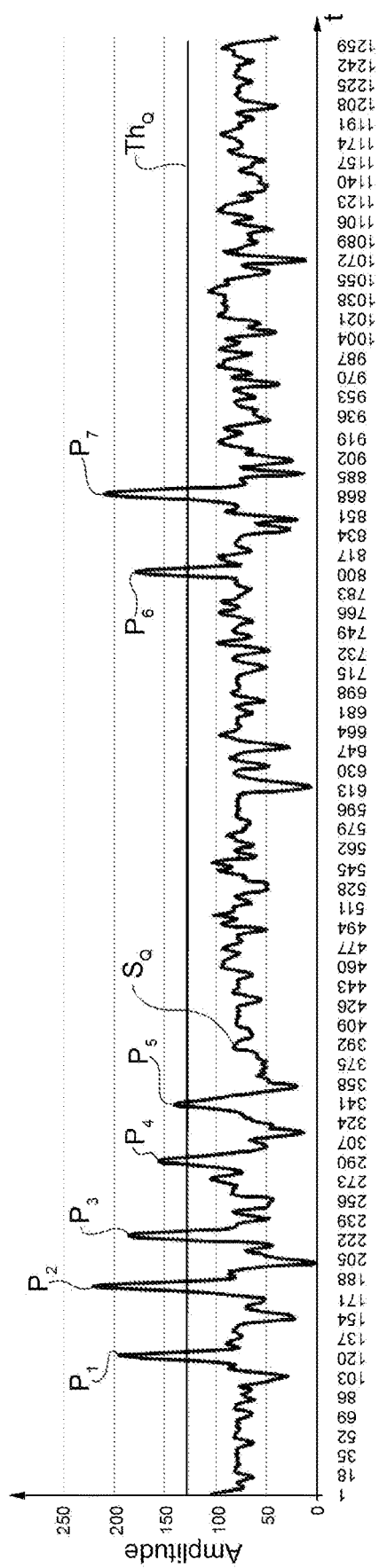
FIG. 3A illustrates a signal generated at output from the sensor for detecting variation of electric charge of FIGS. 1 and 2.
Figure 3B:
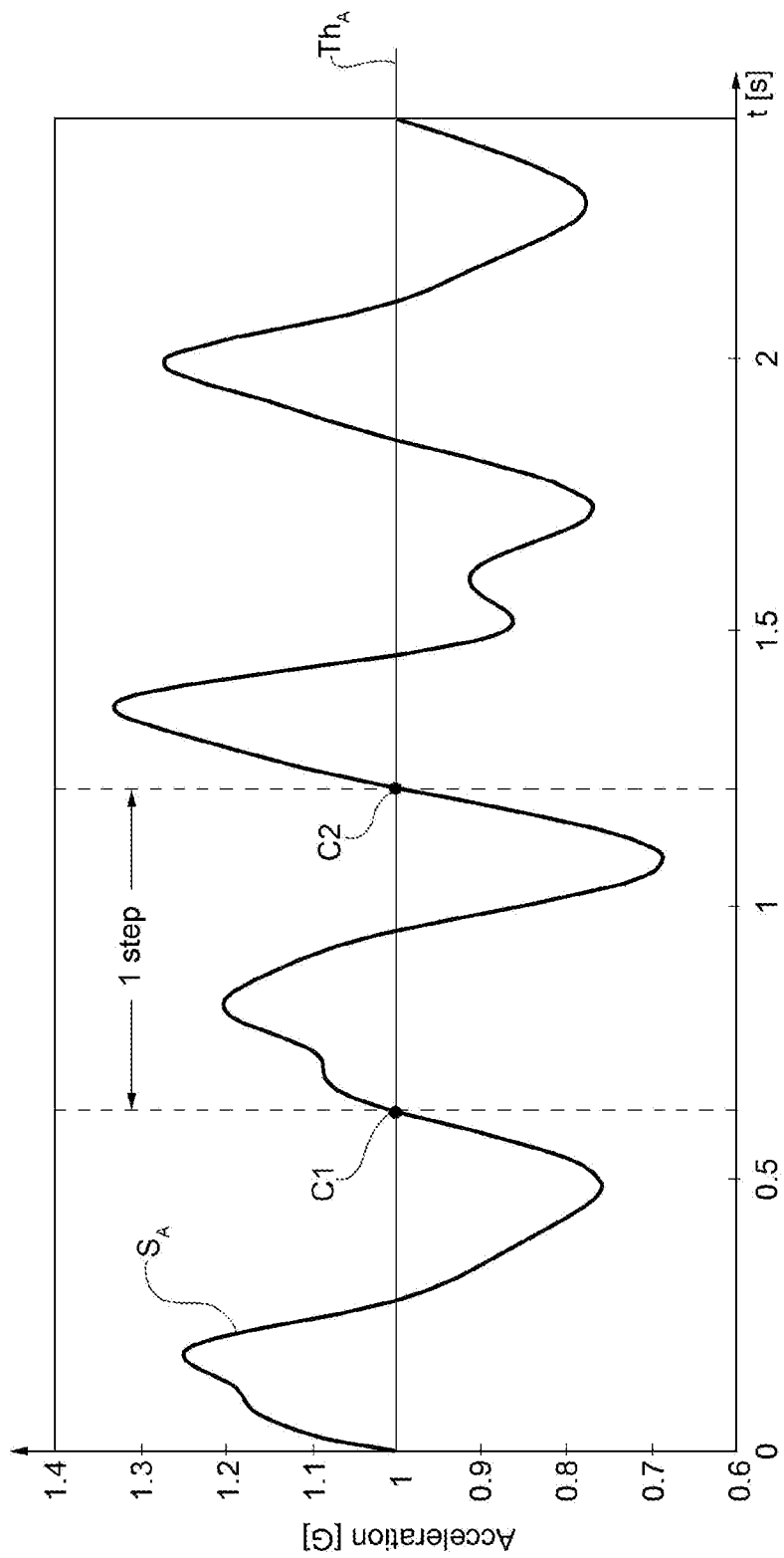
FIG. 3B illustrates a signal generated at output from the accelerometer of FIG. 1.

FIG. 3A illustrates the charge-variation signal $S_Q$ by way of example. As may be noted from FIG. 3A, the charge-variation signal $S_Q$ has a plurality of peaks p1-p7 that follow one another over time (represented by the axis t of the abscissae). Each peak p1-p7 is generated as a consequence of a step detected by the sensor 6 for detecting variation of electrostatic charge according to the variation in electrostatic charge of the user (input signal Vd). In FIG. 3A, the values on the axis of the ordinates are non-dimensional.

As better illustrated hereinafter, the peaks p1-p7 are identified as the components of the charge-variation signal $S_Q$ that overstep a threshold $Th_Q$.

The signal $S_A$, at output from the accelerometer 4, is represented by way of example in FIG. 3B as a function of time t, only relative to a detection axis (e.g., axis Z), and filtered from any possible non-significant frequency components. As may be noted, execution of a step by the user is detected as an increase of the acceleration in a direction (towards the positive values of the axis of the ordinates that represents the amplitude of acceleration, with respect to the stationary value 1G due only to the force of gravity) and by a corresponding acceleration in the opposite direction (towards the negative values of the axis of the ordinates, with respect to the stationary value 1). The dashed lines in FIG. 3B, between the points c1 and c2 of crossing of the threshold 1G, delimit a step. Therefore, as illustrated in FIG. 3B, the plot of the acceleration signal $S_A$ has a given profile of acceleration that repeats at each step (between c1 and c2). In detail, said profile of acceleration comprises in succession: a positive portion in which there is a peak of positive acceleration (i.e., directed upwards), due to resting of the foot and consequent impact on the ground; and a negative portion in which there is a peak of negative acceleration of rebound (i.e., directed downwards), of absolute value lower than the peak of positive acceleration.

Detection of the step is moreover described more fully hereinafter, with reference to step 110 of FIG. 4.

Figure 4:
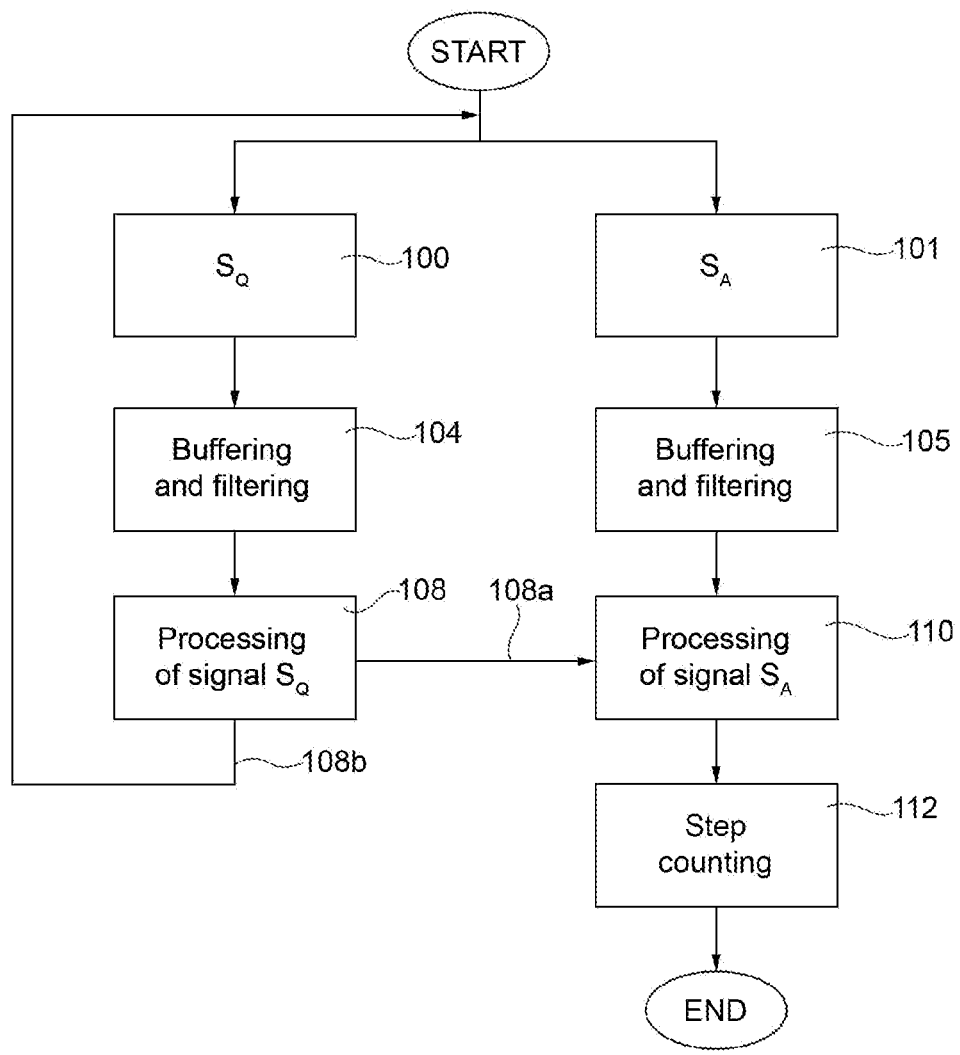
FIG. 4 illustrates, by a block diagram, method implemented by the system for detecting steps of FIG. 1 according to one embodiment of the present disclosure.

FIG. 4 illustrates, by a flowchart, the operations executed by the processing unit 2.

With reference to steps 100 and 101, the processing unit receives, from the sensor 6 for detecting variation of electrostatic charge and from the accelerometer 4, the charge-variation signal $S_Q$ and the acceleration signal $S_A$, respectively. The steps 100 and 101 can be indifferently executed in parallel (simultaneously), or at successive instants in time.

Then, steps 104 and 105, the processing unit 2 carries out respective buffering operations on the signals $S_Q$ and $S_A$ received (saving of the data in a local memory) and filtering (e.g., by a Kalman filter). In particular, filtering has the function of recleaning the signals $S_Q$ and $S_A$ from noise or from components of disturbance at non-significant frequencies (e.g., the mains-supply at 50 Hz or 60 Hz), for example by using low-pass filters. The filters used are configured as a function of the signal to be processed. For instance, step 104 comprises filtering signal components $S_Q$ below 50 Hz; step 105 (optional) comprises filtering, by a low-pass filter (more in particular, with a cutoff frequency of 100 Hz), low-frequency components of the signal $S_A$. In fact, in order to determine execution of the step slowly variable signals are preferable, e.g., of just a few tens of hertz. The signals at higher frequencies are of little significance or may render processing problematical.

Then, step 108, the components of the charge-variation signal $S_Q$ that identify execution of a step by the user are extracted.

For this purpose, the threshold $Th_Q$ (FIG. 3A) is used for identifying the components of the charge-variation signal $S_Q$ that identify a step. In particular, overstepping of the threshold $Th_Q$ by the charge-variation signal $S_Q$ is associated with the execution of a step by the user.

The threshold $Th_Q$ is, in one embodiment, a threshold of a fixed and pre-set type.

In a further embodiment, the threshold $Th_Q$ is of an adaptive type; i.e., it varies as a function of the plot of the charge-variation signal $S_Q$. Calculation of the threshold $Th_Q$ of an adaptive type may be conducted by exploiting techniques known in the art. For instance, it is possible to use sliding windows or overlapping windows. Other techniques for real-time calculation of adaptive threshold may be used.

In an embodiment provided by way of example, the threshold $Th_Q$ is chosen as the mean of the signal $S_Q$ (in the window considered) plus a multiple of the standard deviation of the signal $S_Q$ (in the window considered): $Th_Q$=mean($S_Q$)+n stddev($S_Q$), where n is chosen in the range between 2 and 6, for example 4 (where the term "mean" is used to refer to the operation of calculating the arithmetical mean and "stddev" refers to the operation of calculating the standard deviation).

The time window is, for example, chosen from an appropriate value. Said value depends upon the type of application; the present applicant has found that values compatible with processing on a microcontroller (i.e., taking into account the buffers, the memory used, and the computational resources) range from 2 to 10 s.

In step 108, the signal $S_A$ of the accelerometer 4 is not acquired by the processing unit or, in the case where it was acquired, is not processed for detecting execution of a step or for detecting walking. In other words, during the step 108, identification of the step is made only on the basis of the charge-variation signal $S_Q$.

If at least one step is detected in the charge-variation signal $S_Q$, then step 110 is carried out (arrow 108a at output from block 108); vice versa (arrow 108b at output from block 108), the steps of acquisition of the signals $S_Q$ and $S_A$, storage thereof, conversion into the digital domain and processing of the charge-variation signal $S_Q$ for detecting the step, are repeated. Overstepping of the threshold $Th_Q$ by the charge-variation signal $S_Q$ therefore generates a corresponding trigger signal for starting processing of the acceleration signal $S_A$.

With reference to step 110, the acceleration signal $S_A$ is processed to confirm the presence of the step identified in step 108 on the basis of the signal $S_Q$. Processing of the acceleration signal $S_A$ is executed only when the analysis of the charge-variation signal $S_Q$ at step 108 has yielded positive outcome, i.e., it has identified the presence of at least one step. Vice versa, in the case where the charge-variation signal $S_Q$ is below the threshold $Th_Q$, step 110 is not executed.

Since the charge-variation signal $S_Q$ could be generated and/or received by the processing unit 2 with a certain delay with respect to the signal of the accelerometer (e.g., with a delay of tens or hundreds of milliseconds), according to one aspect of the present disclosure, the processing unit 2 acquires and processes samples of the acceleration signal $S_A$ starting from an instant that precedes overstepping of the threshold $Th_Q$ by the charge-variation signal $S_Q$. This is possible owing to the fact that, as has been said, the acceleration signal $S_A$ is stored (buffered) in a memory in step 105. In particular, the acceleration signal $S_A$ is processed starting from some tens (10-100 ms) or hundreds (100-800 ms) of milliseconds prior to the instant of detection of overstepping threshold $Th_Q$ by the charge-variation signal $S_Q$.

Processing of the acceleration signal $S_A$ to identify the step is carried out according to the prior art, for example as described in the patent Nos. EP1770368 or EP1770369.

With reference to FIG. 3B, the line $Th_A$ corresponds to a constant acceleration of 1G, i.e., to the force of gravity in a static condition of the user, and is used as comparison threshold for detecting the steps made by the user. A step is detected when the measurements of the accelerometer 4, represented by the signal $S_A$, exceed the threshold $Th_A$ (or, in a different but equivalent embodiment, drop below the threshold $Th_A$). For instance, a step may be detected when the measurements of the accelerometer 4 cross the threshold $Th_A$ in points c1 and c2, on a positive or upward slope of the signal $S_A$. Identification of a step therefore corresponds, in this example, to the crossing, by the signal SA, of the threshold $Th_A$ towards values higher than 1G.

As an alternative to what has been previously described (with a constant comparison threshold $Th_A$), it is likewise possible to use a comparison threshold of an adaptive type (for example, a moving-average threshold), as described in the patent application No. US2013/0085711 or in the patent No. EP1770368. For instance, the moving-average threshold adjusts the comparison threshold on the basis of the average of the acceleration detected.

Moreover, as an alternative to the foregoing embodiments, it is likewise possible to perform a frequency analysis, (e.g., by the Fast Fourier Transform, FFT), and apply a threshold in order to detect the frequency components of the signal $S_A$ that exceed said threshold. These components therefore identify execution of a step. An example is illustrated in the patent application No. US2013/0085700. Frequency analysis can be performed on the data of the accelerometer in order to determine, optionally, a dominant frequency usable to select the frequency band of a band-pass filter used for filtering the signal. For instance, if it is found that the dominant frequency is 2 Hz, it is possible to select a filter with a frequency band of 1.5-2.5 Hz to filter the signal. Filtering makes it possible to render the data uniform, for a better analysis and detection of the steps.

Then, step 112 of FIG. 4, if also the check made in step 110 has yielded a positive outcome, the step event is confirmed and a counter is incremented accordingly ($N_S$+1).

Figure 5:
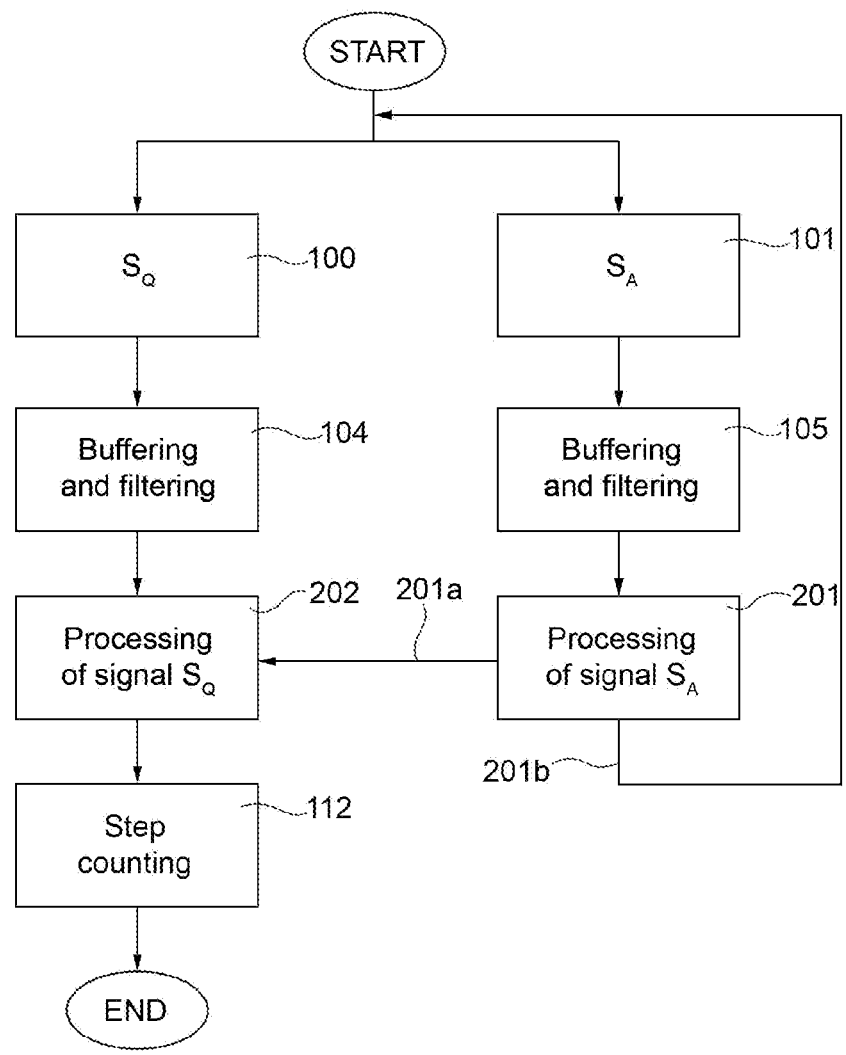
FIG. 5 illustrates, by a block diagram, a method implemented by the system for detecting steps of FIG. 1 according to an embodiment alternative to that of FIG. 4.

FIG. 5 illustrates a further embodiment of the present disclosure, regarding the steps executed by the processing unit 2. FIG. 5 illustrates a block diagram alternative to that of FIG. 4. However, blocks and operations of FIG. 5 that are in common with those of FIG. 4 are identified by the same reference numbers and will not be described any further.

In particular, blocks 100, 101, 104 and 105 are in common with the embodiments of FIGS. 4 and 5.

However, according to the embodiment of FIG. 5, the acceleration signal $S_A$ is always acquired and processed by the processing unit 2 (block 201), for identification of a step according to the prior art (for example, according to the methods already identified previously with reference to block 110 and FIG. 3B).

When said processing confirms that a step has been made by the user, then (output 201a) control passes to block 202, where the charge-variation signal $S_Q$ is acquired and processed. Processing of the charge-variation signal $S_Q$ occurs according to what has already been described with reference to block 108 and to FIG. 3A.

Only if also processing of the charge-variation signal $S_Q$ confirms that a step has been made, does control pass to block 112, where detection of the step is confirmed and the step is counted. Otherwise (output 201b), the step is not confirmed/counted, and the signals $S_A$ and $S_Q$ are again acquired, so that steps of blocks 100 to 105 are repeated.

Figure 6:
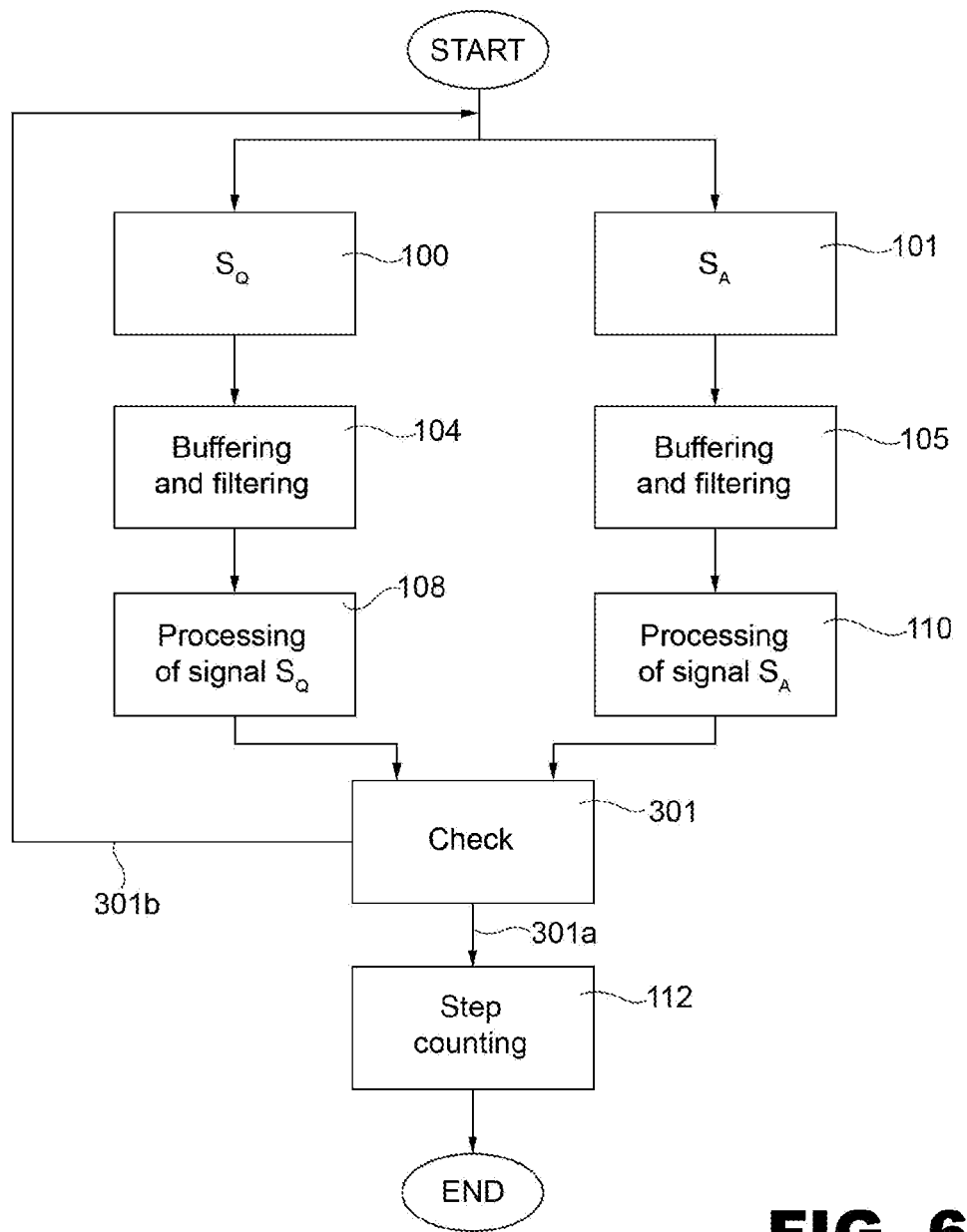
FIG. 6 illustrates, by a block diagram, a method implemented by the system for detecting steps of FIG. 1 according to an embodiment alternative to those of FIG. 4 and FIG. 5.

In a further embodiment, illustrated in FIG. 6 (blocks of FIG. 6 that are in common with those of FIG. 4 are illustrated by the same reference numbers and will not be described any further), the steps of blocks 108 and 110 are executed simultaneously, and the corresponding results (identification of the step in the respective signals $S_Q$ and $S_A$) are sent to the processing unit 2. Then (step 301), the processing unit 2 carries out a check to identify whether, at time instants (or the intervals) corresponding to each other, both of the signals $S_Q$ and $S_A$ identify execution of a step of the user.

Only in the case where both of the signals $S_Q$ and $S_A$ identify a step (datum at output from blocks 108 and 110) does control pass (output 301a) to block 112 where detection of the corresponding step is confirmed and the step is counted. Otherwise (output 301b), the steps 100-110 and 301 already described are repeated.

Figure 7:
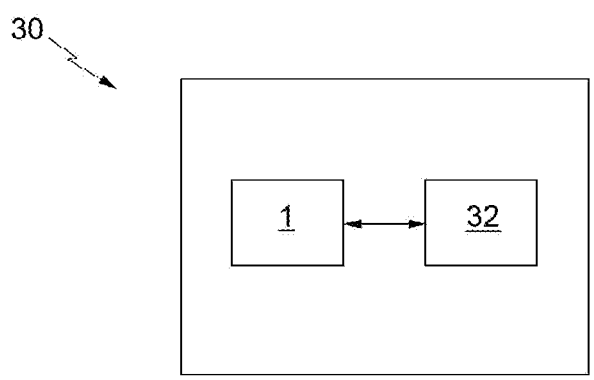
FIG. 7 illustrates a device that includes the system for detecting steps of FIG. 1.

FIG. 7 is a schematic illustration of a portable device 30 (e.g., a pedometer, a smartwatch, a smartphone, etc.) comprising the system 1 of FIG. 1 and, moreover, a graphic user interface 32, connected to the processing unit 2. The graphic user interface 32 displays information at output from the system 1 (in particular, at output from step 108 of FIG. 4), such as, in particular, the number of steps made by the user; it may moreover be used by the user for entering data or issuing commands to the processing unit 2.

Finally, it is evident that modifications and variations may be made to what has been discussed above, without thereby departing from the scope of the present disclosure.

For instance, following upon detection of the peaks p1-p7 in the signal of FIG. 3A, the further step of recognizing a specific shape of such peak (or, rather, of the signal $S_Q$ in a time interval that comprises said peak) can be carried out. For instance, it is possible to use machine-learning and/or artificial-intelligence techniques for automatic recognition of specific patterns of the signal $S_Q$ associated with a step made by the user so as to discriminate between different types of step, amongst which, for example, a step forward, a step backward, a step up, a step down, the sound of a footstep on the ground in the absence of displacement of the user, etc.

As an alternative, machine-learning and/or artificial-intelligence techniques may be used for automatic recognition of specific patterns of the signal $S_Q$ associated with a step made by the user as an alternative to the use of the threshold $TH_Q$, in order to identify the presence of a step in the signal $S_Q$ and/or the type of step.

Likewise, algorithms of automatic pattern recognition associated with a step made by the user may be used for identifying the presence of a step and/or the type of step in the acceleration signal $S_A$.

Moreover, it may be noted that it is possible to use a charge-variation sensor of a type that cannot be worn by the user, but is configured to detect, at a distance, electrostatic variations generated following upon execution of a step by the user. In this case, only the accelerometer 4 is carried by the user, for detection of the steps made by him. A system of this type is a distributed system and may be used, for example, in applications of gaming or enhanced reality, in which the user performs his own movements in a circumscribed environment, for example a room.

The advantages achieved by the present disclosure are evident from the foregoing description.

In particular, the present disclosure reduces considerably the false positives in counting of steps of the user of the system, in so far as it envisages a double validation for the confirmation of the step made.

In addition, since according to the embodiment of FIG. 4 identification of the step is made first by analyzing the charge-variation signal $S_Q$, the result of this analysis determining a consequent processing of the signal $S_A$ of the accelerometer (which otherwise would not be processed), there is a considerable saving in computational resources and consumption levels, in so far as the signal of the accelerometer is processed only when necessary.

Likewise, with reference to FIG. 5, since identification of the step is made first by analyzing the acceleration signal $S_A$, which determines a consequent processing of the charge-variation signal $S_Q$ (which otherwise would not be processed), there is a considerable saving of computational resources and consumption levels, in so far as the signal of the sensor 6 is processed only when necessary and to confirm the data provided by the accelerometer 4.

Consequently, in both of the embodiments of FIGS. 4 and 5, an increase in reliability of the step-detection/counting system is obtained and, simultaneously, an optimization of energy efficiency.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for detecting a step of a user, comprising:
   processing circuitry;
   a sensor coupled to the processing circuitry and configured to detect a variation of electrostatic charge of the user during execution of a step by the user and generate a charge-variation signal; and
   an accelerometer coupled to the processing circuitry and configured to detect an acceleration as a consequence of the step of the user and generate an acceleration signal,
   wherein the processing circuitry is configured to:
   acquire the charge-variation signal;
   acquire the acceleration signal;
   detect, in the charge-variation signal, a first charge-variation characteristic identifying the step of the user;
   detect, in the acceleration signal, a second acceleration signal characteristic identifying the step of the user, wherein one of the first characteristic and the second characteristic is detected prior to detecting the other of the first characteristic and the second characteristic, and the other of the first characteristic and second characteristics is detected only in a case where the one of the first characteristic and the second characteristic has been detected; and
   validate the execution of the step by the user in response to detecting both the first and the second characteristics.

2. The system according to claim 1, wherein the processing circuitry is configured to detect the first charge-variation characteristic prior to detecting the second acceleration signal characteristic, and the processing circuitry is configured to detect the second acceleration signal characteristic only in a case where the first charge-variation characteristic has been detected.

3. The system according to claim 1, wherein the processing circuitry is configured to detect the second acceleration signal characteristic prior to detecting the first charge-variation characteristic, and the processing circuitry is configured to detect the first charge-variation characteristic only in the case where the second acceleration signal characteristic has been detected.

4. The system according to claim 1, wherein the processing circuitry is configured to process the acceleration signal or the charge-variation signal using machine-learning or artificial-intelligence algorithms for identifying a type of step, the type of step including at least one of: a step forward, a step backward, a step up, a step down, or a sound of a footstep on the ground in the absence of displacement of the user.

5. The system according to claim 1, wherein the detecting the first charge-variation characteristic includes at least one of: detecting a peak of the charge-variation signal that exceeds a fixed threshold; detecting a peak of the charge-variation signal that exceeds an adaptive threshold; or detecting specific patterns of the charge-variation signal by machine-learning or artificial-intelligence algorithms.

6. The system according to claim 5, wherein the detecting a peak of the charge-variation signal that exceeds an adaptive threshold includes:
   calculating a mean value assumed by the charge-variation signal in a time interval;
   calculating a coefficient of standard deviation of the charge-variation signal in the time interval; and
   adding the mean value to a multiple of the coefficient of standard deviation.

7. The system according to claim 1, wherein the detecting the second acceleration signal characteristic includes at least one of: detecting a peak of the acceleration signal that exceeds a fixed threshold; detecting a peak of the acceleration signal that exceeds an adaptive threshold; or executing a frequency analysis of the acceleration signal.

8. The system according to claim 1, wherein the sensor is configured to be worn by the user in direct electrical contact with a body portion of the user and includes an instrumentation amplifier and an analog-to-digital converter coupled at an output of the instrumentation amplifier.

9. The system according to claim 1, configured to be worn by the user.

10. The system according to claim 1, wherein the validating the execution of the step by the user includes incrementing a counter of a number of steps made by the user.

11. The portable electronic device of claim 1, comprising at least one of: a pedometer, a smartwatch, or a smartphone.

12. A method for detecting a step of a user, comprising:
supplying a charge-variation signal by a sensor configured to detect a variation of electrostatic charge of the user during the execution of a step by the user;
supplying an acceleration signal by an accelerometer coupled to processing circuitry and configured to detect an acceleration as a consequence of the step of the user;
detecting, in the charge-variation signal, a first charge-variation characteristic identifying the step of the user;
detecting, in the acceleration signal, a second acceleration signal characteristic identifying the step of the user, wherein one of the first characteristic and the second characteristic is detected prior to detecting the other of the first characteristic and the second characteristic, and the other of the first characteristic and second characteristics is detected only in a case where the one of the first characteristic and the second characteristic has been detected; and
validating the execution of the step by the user in response to detecting both of the first and second characteristics.

13. The method according to claim 12, wherein the detecting the first charge-variation characteristic is executed prior to the detecting the second acceleration signal characteristic, and the detecting the second acceleration signal characteristic is executed only in the case where the first charge-variation characteristic has been detected.

14. The method according to claim 12, wherein the detecting the second acceleration signal characteristic is executed prior to the detecting the first charge-variation characteristic, and the detecting the first charge-variation characteristic is executed only in the case where the second acceleration signal characteristic has been detected.

15. The method according to claim 12, comprising:
processing the acceleration signal or the charge-variation signal by machine-learning or artificial-intelligence algorithms for identifying a type of step, the type of step including at least one of: a step forward, a step backward, a step up, a step down, or a sound of a footstep on the ground in the absence of displacement of the user.

16. The method according to claim 12, wherein the detecting the first charge-variation characteristic includes at least one of: detecting a peak of the charge-variation signal that exceeds a fixed threshold; detecting a peak of the charge-variation signal that exceeds an adaptive threshold; or detecting specific patterns of the charge-variation signal by machine-learning or artificial-intelligence algorithms.

17. The method according to claim 16, wherein the detecting a peak of the charge-variation signal that exceeds an adaptive threshold comprises:
calculating a mean value assumed by the charge-variation signal in a time interval;
calculating a coefficient of standard deviation of the charge-variation signal in the time interval; and
adding the mean value to a multiple of the coefficient of standard deviation.

18. The method according to claim 12, wherein the detecting the second acceleration signal characteristic includes at least one of: detecting a peak of the acceleration signal that exceeds a fixed threshold; detecting a peak of the acceleration signal that exceeds an adaptive threshold; or executing a frequency analysis of the acceleration signal.

19. The method according to claim 12, wherein the validating the execution of the step by the user includes incrementing a counter of a number of steps made by the user.

20. A device, comprising:
a memory; and
processing circuitry coupled to the memory, wherein the processing circuitry, in operation:
detects, in a charge-variation signal, a first charge-variation characteristic identifying a user-step;
detects, in an acceleration signal, a second acceleration signal characteristic identifying the user-step, wherein one of the first characteristic and the second characteristic is detected prior to detecting the other of the first characteristic and the second characteristic, and the other of the first characteristic and second characteristics is detected only in a case where the one of the first characteristic and the second characteristic has been detected; and
in response to detecting both the first and the second characteristics, detects the user-step.

21. The device according to claim 20, wherein the processing circuitry, in operation, detects the first charge-variation characteristic prior to detecting the second acceleration signal characteristic.

22. The device according to claim 20, wherein the processing circuitry, in operation, detects the second acceleration signal characteristic prior to detecting the first charge-variation characteristic.

23. The device according to claim 20, wherein the processing circuitry, in operation, in response to detecting a step, identifies a type of step.

24. The device according to claim 20, wherein the processing circuitry, in operation, counts a number of detected steps.

25. The device according to claim 20, comprising one or more sensors coupled to the processing circuitry, wherein the one or more sensors, in operation, generate the charge-variation signal and the acceleration signal.

26. A non-transitory computer-readable medium having contents which cause a processing device to perform a method, the method comprising:
detecting, in a charge-variation signal, a first charge-variation characteristic identifying a user-step;
detecting, in an acceleration signal, a second acceleration signal characteristic identifying the user-step, wherein one of the first characteristic and the second characteristic is detected prior to detecting the other of the first characteristic and the second characteristic, and the other of the first characteristic and second characteristics is detected only in a case where the one of the first characteristic and the second characteristic has been detected; and
in response to detecting both the first and the second characteristics, detecting the user-step.

27. The non-transitory computer-readable medium of claim 26, wherein the contents comprise instructions executed by the processing device.

28. The non-transitory computer-readable medium of claim 26, wherein the method comprises counting a number of detected steps.

29. The non-transitory computer-readable medium of claim 26, wherein the method comprises generating the charge-variation signal and the acceleration signal.

* * * * *